United States Patent [19]

Sitzmann

[11] Patent Number: 5,241,071

[45] Date of Patent: Aug. 31, 1993

[54] 2-POLYNITROALKYL-5-PERFLUOROALKYL-1,3,4-OXADIAZOLES

[75] Inventor: Michael E. Sitzmann, Adelphi, Md.

[73] Assignee: The United States of America as represented by the Secretary of the Navy, Washington, D.C.

[21] Appl. No.: 901,621

[22] Filed: Jun. 15, 1992

[51] Int. Cl.$^5$ .................................. C07D 271/10
[52] U.S. Cl. .................................................. 548/143
[58] Field of Search ........................................ 548/143

[56] References Cited

PUBLICATIONS

Vigalok, Khim. Geterotsikl. Soedin. 1975 (5) 713.

Primary Examiner—Robert Gerstl
Attorney, Agent, or Firm—John D. Lewis; Roger D. Johnson

[57] ABSTRACT

An oxadiazole of the formula

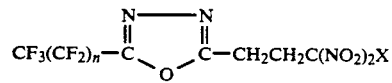

wherein n is 0, 1, 2, 3, or 4 when X is —F but n is 0, 1, or 2 when X is —NO$_2$. These oxidiazoles are useful as energetic plasticizers for explosives.

11 Claims, No Drawings

2-POLYNITROALKYL-5-PERFLUOROALKYL-1,3,4-OXADIAZOLES

BACKGROUND OF THE INVENTION

This invention relates to plasticizers and more particularly to energetic plasticizers for plastic bonded explosives.

A number of new fluorinated binders [for example, perfluoroalkyl polyformals as described by H. G. Adolph and J. M. Goldwasser; U.S. Pat. No. 4,740,579 (1988) and U.S. Pat. No. 4,740,628 (1988)] have recently become available and energetic formulations that contain these new fluorinated binders along with nitro oxidizers/explosives (HMX, for example) have been prepared. These new highly fluorinated binders exhibit quite different chemical properties compared to the nitro oxidizers/explosives. Because of these differences in properties, the usual nitro plasticizers (FEFO, NG, TMETN) used in the formulations are attracted toward the nitro oxidizer/explosive and not the fluorinated binder. These differences in the attraction of the nitro plasticizer for the binder and oxidizer can cause the plasticizer to migrate during storage of the formulations.

It would be desirable to have an energetic plasticizier that would not migrate as much as present energetic plasticizers.

SUMMARY OF THE INVENTION

Accordingly, an object of this invention is to provide new energetic plasticizers.

Another object of this invention is to provide new energetic plasticizers which are attracted by both nitro compounds and fluoro compounds.

A further object of this invention is to provide new energetic plasticizers with less tendency to migrate in plastic bonded explosives with fluoro polymer binders and nitro explosive fills.

These and other objects of this invention are accomplished by providing:

Oxadiazoles of the formula

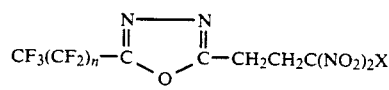

wherein X is $-NO_2$ or $-F$ and wherein if X is $-NO_2$, then n is 0, 1, or 2, but if X is -F, then n is 0, 1, 2, 3, or 4.

These oxadiazoles are prepared by the following reaction sequence:

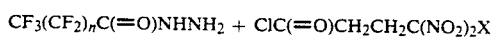

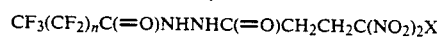

 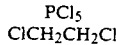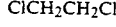

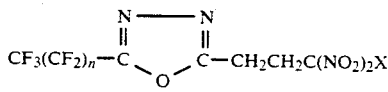

wherein X and n are defined above.

The oxadiazoles of this invention are useful as energetic plasticizers for plastic bonded explosives made from fluoropolymers and nitro organic and inorganic explosive fills.

DETAILED DESCRIPTION OF THE PREFERRED EMBODIMENT

The high energy plasticizers of this invention may be represented by the formula

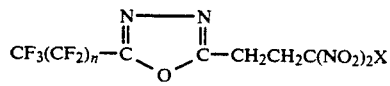

where X is either a nitro group ($-NO_2$) or a fluorine atom ($-F$). If X is $-NO_2$, then n is preferably 0, 1, or 2. However, if X is $-F$, then n is preferably 0, 1, 2, 3, or 4.

Specifically, the preferred energetic plasticizers (oxaiazoles) are:

(1) 2-(3,3,3-trinitropropyl)-5-(trifluoromethyl)-1,3,4-oxadiazole (with $X=-NO_2$ and $n=0$);
(2) 2-(3,3,3-trinitropropyl)-5-(perfluoroethyl)-1,3,4-oxadiazole (with $X=-NO_2$ and $n=1$);
(3) 2-(3,3,3-trinitropropyl)-5-(perfluoropropyl)-1,3,4-oxadiazole (with $X=-NO_2$ and $n=2$);
(4) 2-(3-fluoro-3,3-dinitropropyl)-5-(trifluoromethyl)-1,3,4-oxadiazole (with $X=-F$ and $n=0$);
(5) 2-(3-fluoro-3,3-dinitropropyl)-5-(perfluoroethyl)-1,3,4-oxadiazole (with $X=-F$ and $n=1$);
(6) 2-(3-fluoro-3,3-dinitropropyl)-5-(perfluoropropyl)-1,3,4-oxadiazole (with $X=-F$ and $n=2$);
(7) 2-(3-fluoro-3,3-dinitropropyl)-5-(perfluorobutyl)-1,3,4-oxadiazole (with $X=-F$ and $n=3$); or
(8) 2-(3-fluoro-3,3-dinitropropyl)-5-(perfluoropentyl)-1,3,4-oxadiazole (with $X=-F$ and $n=4$).

The preferred values of n are selected for $X=-NO_2$ and for $X=-F$ to specify compounds that have melting points that make them suitable for use as plasticizers.

These plasticizer molecules have 3 distinct parts At one end of the molecule is a perfluoroalkyl group such as $-CF_3$, $-CF_2CF_3$, $-CF_2CF_2CF_3$, $-CF_2CF_2CF_2CF_3$, $-CF_2CF_2CF_2CF_2CF_3$, etc. At the other end of the molecule is a polynitroalkyl group such as $-CH_2CH_2C(NO_2)_3$, $-CH_2CH_2CF(NO_2)_2$, etc. At the center of the molecule, separating these two distinct end groups, is a bulky 1,3,4-oxadiazole group,

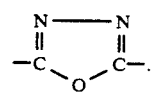

All of this enhances the attraction of the energetic plasticizer for both the polyfluoro binder polymer and for the very different nitro groups on the explosive filler. As a result, migration of the plasticizer away from either the binder or the explosive filler is greatly reduced.

The energetic plasticizers (oxadiazoles) are prepared by the following reaction sequence:

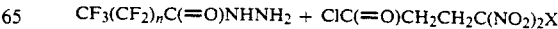

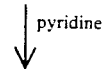

-continued $$CF_3(CF_2)_nC(=O)NHNHC(=O)CH_2CH_2C(NO_2)_2X$$

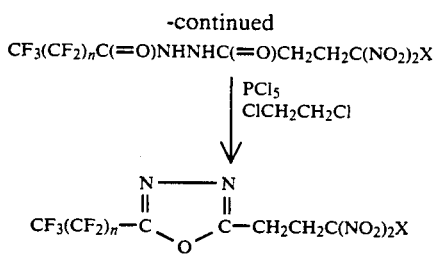

wherein X and n are as defined above.

These preferred oxadiazoles (1 through 8) are prepared from the corresponding N-(polynitroacyl)-N'-(perfluoroacyl)hydrazines:

(1A) N-(4,4,4-trinitrobutyryl)-N'-(trifluoroacetyl)hydrazine,
$CF_3C(=O)NHNHC(=O)CH_2CH_2C(NO_2)_3$;

(2A) N-(4,4,4-trinitrobutyryl)-N'-(perfluoropropionyl)hydrazine,
$CF_3CF_2C(=O)NHNHC(=O)CH_2CH_2C(NO_2)_3$;

(3A) N-(4,4,4-trinitrobutyryl)-N'-(perfluorobutyryl)hydrazine
$CF_3CF_2CF_2C(=O)NHNHC(=O)CH_2CH_2C(NO_2)_3$;

(4A) N-(4-fluoro-4,4-dinitrobutyryl)-N'-(trifluoroacetyl)hydrazine,
$CF_3C(=O)NHNHC(=O)CH_2CH_2CF(NO_2)_2$;

(5A) N-(4-fluoro-4,4-dinitrobutyryl)-N'-(perfluoropropionyl)hydrazine,
$CF_3CF_2C(=O)NHNHC(=O)CH_2CH_2CF(NO_2)_2$;

(6A) N-(4-fluoro-4,4-dinitrobutyryl)-N'-(perfluorobutyryl)hydrazine,
$CF_3CF_2CF_2C(=O)NHNHC(=O)CH_2CH_2CF(NO_2)_2$;

(7A) N-4-fluoro-4,4-dinitrobutyryl)-N'-(perfluoropentanoyl)hydrazine
$CF_3CF_2CF_2CF_2C(=O)NHNHC(=O)CH_2CH_2CF(NO_2)_2$; or (8A) N-(4-fluoro-4,4-dinitrobutyryl)-N'-(perfluorohexanoyl)hydrazine,
$CF_3CF_2CF_2CF_2CF_2C(=O)NHNHC(=O)CH_2CH_2CF(NO_2)_2$ by cyclization of the hydrazine (1A through 8A) using phosphorus pentachloride in refluxing 1,2-dichloroethane. Examples 2,4,6,8,10, and 12 illustrate this cyclization reaction.

The selected N-(polynitroacyl)-N'-(perfluoroacyl)-hydrazine is prepared by condensing a
perfluoroacyl hydrazine that is N-(trifluoroacetyl)hydrazine,
$CF_3C(=O)NHNH_2$;
N-(perfluoropropionyl)hydrazine,
$CF_3CF_2C(=O)NHNH_2$;
N-(perfluorobutyryl)hydrazine,
$CF_3CF_2CF_2C(=O)NHNH_2$; or
N-(perfluoropentanoyl)hydrazine,
$CF_3CF_2CF_2CF_2C(=O)NHNH_2$;
with a polynitroacyl chloride that is
4,4-trinitrobutyryl chloride,
$ClC(=O)CH_2CH_2C(NO_2)_3$; or
4-fluoro-4,4-fluoro-4,4-dinitrobutyryl chloride,
$ClC(=O)CH_2CH_2CF(NO_2)_2$.

Pyridine is added to the reaction mixture to neutralize the hydrochloric acid that is liberated during the reaction. This reaction is illustrated by examples 1, 3, 5, 7, 9, and 11.

The preparation of perfluoroacyl hydrazines, $CF_3(CF_2) C(=O)NHNH_2$, have been described by H. C. Brown et al. *Journal of Organic Chemistry*, 26(11), P. 4407 (1961), herein incorporated in its entirety. Their procedures were repeated to produce $CF_3CF_2C(=O)NHNH_2$ and $CF_3CF_2CF_2C(=O)NHNH_2$. The perfluoroacyl hydrazine $CF_3CF_2CF_2CF_2CF_2CF_2C(=O)NHNH_2$ was not reported but this material (mp 103°–104° C.) was easily formed by applying their method. For $CF_3C(=O)NHNH_2$, they report a melting point of 143°–144° C. but this is apparently an error. The melting point for this compound was found to be 42°–43° C. and was prepared as follows: To 4.5 g (0.032 mole) of ethyl trifluoroacetate stirred in an ice bath was added 1.0 g (0.032 mole) of anhydrous hydrazine (95% min) in 3 mL of methanol. After 16 hours at room temperature, methylene chloride (15 mL) was added and the volatiles were removed by distillation (bath temperature was eventually raised to 100° C. and held until distillation stopped). After cooling, 20 mL of methylene chloride was added and the mixture was stirred to produce an insoluble solid. The solid (mp 128°–133° C.) was removed and the filtrate was cooled to −20° C. to give 1.7 g, mp 35°–38° C. Recrystallization from methylene chloride gave 1.1 g of N-(trifluroacetyl)hydrazine, mp 42°–43° C.

The 4,4,4-trinitrobutyryl chloride (Chemical Abstract Number 36638-86-5) starting material was prepared by refluxing 4,4,4-trinitrobutyric acid with an excess of thionyl chloride for 20 hours before the mixture was concentrated in vacuo and the product distilled as taught by Marvin H. Gold, et al. in an article titled, "Preparation of Aliphatic gem-Dinitro Monoisocyanates and Derivatives," *Journal of Organic Chemistry* (1962), volume 27, pages 334–335, at page 334, column 2, herein incorporated by reference in its entirety.

The 4-fluoro-4,4-trinitrobutyryl chloride starting material can be prepared in a similar manner. 4-Fluoro-4,4-dinitrobutyric acid is added in portions with stirring to an excess of thionyl chloride at 18°–20° C. The homogeneous solution formed is then heat slowly to boiling where it is kept for about 2 hours. The excess thionyl chloride is then distilled off. The 4-fluoro-4,4-trinitrobutyryl chloride product is then distilled off under vacuum. This procedure was taught by L. T. Eeremenko et al. *Izvestlya Akademil Nauk SSR, Seriya Khimicheskaya* No. 6, pp 1331–1336 June, 1969.

The general nature of the invention having been set forth, the following examples are presented as specific illustrations thereof. It will be understood that this invention is not limited to these specific examples, but is susceptible to various modifications that will be recognized by one of ordinary skill in the art.

EXAMPLE 1

N-(4,4,4-Trinitrobutyryl)-N'-(perfluorooctanoyl)hydrazine

To a stirred solution of 0.9 g (0.0036 mole) of 4,4,4-trinitrobutyryl chloride in 15 mL of anhydrous diethyl ether at 25° C. was added 1.05 g (0.0025 mole) of N-(perfluorooctanoyl) hydrazine. Pyridine (0.3 mL) was added dropwise and stirring was continued for 10 minutes until the insoluble material turned mostly solid. Dilute hydrochloric acid (5%) (10 mL) was added, the ether solution was separated, dried ($Na_2SO_4$), and the volatiles were removed. The semisolid residue was stirred with dilute sodium bicarbonate to give 1.6 g of insoluble solid, mp 102°–106° C. Crystallization from 1,2-dichloroethane gave the product, N-(4,4,4-trinitrobutyryl)-N'-(perfluorooctanoyl)hydrazine, 0.95 g (61%), mp 123°–125° C. $^1$H NMR (acetone-$d_6$+$D_2O$): 2.97 (t, 2H), 3.85 (t, 2H); IR (KBr): 3250 (NH), 1740, 1760 (C=O), 1610 ($NO_2$), 1250-1200, 1150 (C-F). Anal. Calcd for $C_{12}H_6F_{15}N_5O_8$: C, 22.76; H, 0.96; F, 45.01; N, 11.06. Found: C, 22.65; H, 1.00; F, 44.70; N, 11.18.

EXAMPLE 2

2-(3,3,3-Trinitropropyl)-5-(perfluoroheptyl)-1,3,4-oxadiazole

A mixture of 0.47 g (0.74 mmole) of N-(4,4,4-trinitrobutyryl)-N'-(perfluorooctanoyl)hydrazine and 0.065 g (0.003 mole) of phosphorus pentachloride in 8 mL of 1,2-dichloroethane was heated at reflux temperature for 4 hours. The volatiles were removed to give a solid, which was washed with water, and then chromatographed on Silica gel 60 ($CH_2Cl_2$ as eluent) to give the product 2-(3,3,3-trinitropropyl)-5-(perfluoroheptyl)-1,3,4-oxadiazole, 0.35 g (78%), mp 70-71° C; $^1$H NMR (acetone-$d_6$) 3.83 (m, 2H), 4.23 (m, 2H); IR (KBr): no NH or C=O; 1620, 1605 ($NO_2$), 1250-1140 (C-F).

Anal. Calcd for $C_{12}H_4F_{15}N_5O_7$: C, 23.43; H, 0.66; F, 46.33; N, 11.38.

Found: C, 23.26, H, 0.66; F, 47.59; N, 11.44.

EXAMPLE 3

N-(4,4,4-Trinitrobutyryl)-N'-(perfluorobutyryl)hydrazine (3A)

To a solution of 1.0 g (0.0041 mole) of 4,4,4-trinitrobutyryl chloride in anhydrous diethyl ether (10 mL) stirred at 20° C. (water bath) was added 0.9 g (0.0039 mole) of N-(heptafluorobutyryl)hydrazine. The mixture became thick with precipitate and sufficient ether (10 mL) was added to allow efficient stirring. Pyridine (0.35 ml, 0.0044 mole) was added dropwise and the mixture was stirred for 5 minutes before 5% hydrochloric acid (10 mL) was added. The ether layer was dried ($Na_2SO_4$), the volatiles were removed, and the residue was stirred with water to give 1.5 g, mp 146°–150° C. Crystallization from 1,2-dichloroethane gave the product, N-(4,4,4-trinitrobutyryl)-N'-(perfluorobutyryl)hydrazine, 1.2 g (70%) mp 154°–156° C.; $^1$H NMR (acetone-$d_6$+$D_2O$): 2.98 (t, 2H), 3.87 (t, 2H).

EXAMPLE 4

2-(3,3,3-Trinitropropyl)-5-(perfluoropropyl)-1,3,4-oxadiazole (3)

Phosphorus pentachloride (1.2 g, 0.0057 mole) and N-(4,4,4-trinitrobutyryl)-N'-(perfluorobutyryl)hydrazine (0.8 g, 0.0018 mole) in 10mL of dichloroethane was held at reflux temperature for 4 hours. Removal of volatiles 9ave an oil which was washed with water and then chromatographed on Silica gel 40 ($CH_2Cl_2$ as eluent) to give 0.5 g (66%) of 2-(3,3,3-trinitropropyl)-5-(perfluoropropyl)-1,3,4-oxadiazole, mp 43°–45° C.; $^1$H NMR (acetone): 3.84 (m, 2H), 4.23 (m, 2H). Anal. Calcd for $C_8H_4F_7N_5O_7$: C, 23.14; H, 0.97; F, 32.04; N, 16.87. Found: C, 23.07; H, 1.00; F, 31.80; N, 16.95.

EXAMPLE 5

N-(4 4,4-Trinitrobutyryl)-N'-(perfluoropropionyl)hydrazine (2A)

A mixture formed by adding 0.77 g (0.0043 mole) of N-(perfluoropropionyl)hydrazine to a solution of 1.05 g (0.0043 mole) of 4,4,4-trinitrobutyryl chloride in 30 mL of anhydrous diethyl ether was stirred at 20° C during the dropwise addition of 0.35 mL of pyridine. After 5 minutes, dilute hydrochloric acid (10 mL) was added, and the ether layer was separated and dried ($MgSO_4$). Removal of volatiles gave a semisolid which was stirred with dilute sodium bicarbonate to give 1.0 g, mp 105°–118° C. Crystallization from 1,2-dichloroethane gave the product, N-(4,4,4-trinitrobutyryl)-N'-(perfluoropropionyl)hydrazine, 0.65 g (41%), mp 123°–125° C.; $^1$H NMR (acetone-$d_6$+$D_2O$): 2.95 (t, 2H); 3.85 (t, 2H).

EXAMPLE 6

2-(3,3,3-Trinitropropyl)-5-(perfluoroethyl)-1,3,4-oxadiazole (2)

A solution containing 0.6 g (0.0016 mole) of N-(4,4,4-trinitrobutyryl)-N'-(perfluoropropionyl)hydrazine and 0.8 g (0.0038 mole) of phosphorus pentachloride in 7 mL of 1,2-dichloroethane was held at reflux temperature for 4 hours before the volatiles were removed to give an oil residue. The residue was dissolved in $CH_2Cl_2$, washed with water, and chromatographed on Silica gel 40 ($CH_2Cl_2$ as eluent) to give the product, 2-(3,3,3-trinitropropyl)-5-(perfluoroethyl)-1,3,4-oxadiazole, 0.4 g (70%), mp 36°–38° C. $^1$H NMR (acetone-$d_6$): 3.80 (m, 2H), 4.20 (m, 2H).

Anal. Calcd for $C_7H_4F_5N_5O_7$: C, 23.03; H, 1.10; F, 26.02; N, 19.18. Found: C, 23.01; H, 1.10; F, 24.15; N, 19.58.

EXAMPLE 7

N-(4,4,4-Trinitrobutyryl)-N'-(trifluoroacetyl)hydrazine (1A)

To 1.65 g (0.007 mole) of 4,4,4-trinitrobutyryl chloride in 15 mL of anhydrous diethyl ether stirred in a water bath at 15° C. was added 0.9 g (0.007 mole) of N-(trifluoroacetyl)hydrazine. Pyridine (0.6 mL, 0.007 mole) was added dropwise. After 3 minutes, dilute hydrochloric acid was added and the ether layer was separated and dried ($Na_2SO_4$). The volatiles were removed and the residue was stirred with water and then with $CH_2Cl_2$ to give the product N-(4,4,4-trinitrobutyryl)-N'-(trifluoroacetyl)hydrazine, 1.15 g (50%), mp 154°–156° C. Crystallization from 1,2-dichloroethane raised the melting point to 157°–159° C.; $^1$H NMR (acetone-$d_6$+$D_2O$): 2.97 (t, 2H), 3.86 (t, 2H); IR (KBr): 3330, 3220 (NH), 1745, 1690 (C=O); 1610, 1590 ($NO_2$); 1195 (C—F).

EXAMPLE 8

2-(3,3,3-Trinitropropyl)-5-(trifluoromethyl)-1,3,4-oxadiazole (1)

Phosphorus pentachloride (0.65 g, 0.003 mole) and N-(4,4,4-trinitrobutyryl)-N'-(trifluoroacetyl)hydrazine (0.7 g, 0.002 mole) in 7 mL of 1,2-dichloroethane was held at reflux temperature for 4 hours. Removal of volatiles gave an oil residue which as dissolved in $CH_2Cl_2$, washed with water, and dried ($Na_2SO_4$). Chromatography on Silica gel 40 (CH$_2$Cl$_2$ as eluent) gave 0.4 g (63%) of an oil which was cooled to give solid 2-(3,3,3-trinitropropyl)-5-(trifluoromethyl)-1,3,4-oxadiazole, mp 18°–19° C.; $^1$H NMR (acetone-d$_6$): 3.80 (m, 2H), 4.20 (m, 2H).

Anal. Calcd for C$_6$H$_4$F$_3$N$_5$O$_7$: C, 22.87; H, 1.28; F, 18.09; N, 22.22. Found: C, 22.77; H, 1.15; F, 17.71; N, 21.93.

EXAMPLE 9

N-(4-Fluoro-4,4-dinitrobutyryl)-N'-(perfluorobutyryl)-hydrazine (6A)

A thick mixture was formed after 1.0 g (0.0044 mole) of N-(perfluorobutyryl)hydrazine was added to a solution of 0.95 g (0.0044 mole) of 4-fluoro-4,4-dinitrobutyryl chloride in 20 mL of anhydrous diethyl ether stirred at 20° C. Pyridine (0.4 mL, 0.005 mole) was added dropwise and, after 5 minutes, dilute hydrochloric acid (10 mL) was added. The ether layer was dried (Na$_2$SO$_4$) before the volatiles were removed and the residue was stirred with dilute sodium bicarbonate to give 1.35 g (76%), mp 138°–142° C. Crystallization from 1,2-dichloroethane gave the product N-(4-fluoro-4,4-dinitrobutyryl)-N'-(perfluorobutyryl)hydrazine, 1.24 g, mp 143-144° C; $^1$H NMR (acetone-d$_6$+D$_2$O): 2.80 (t, 2H), 3.36, 3.58 (d of t, 2H).

EXAMPLE 10

2-(3-Fluoro-3,3-dinitropropyl)-5-(perfluoropropyl)-1,3,4-oxadiazole (6)

Dichloroethane (8 mL) containing 0.8 g (0.002 mole) of N-(4-fluoro-4,4-dinitrobutyryl)-N'-(perfluorobutyryl)hydrazine and 1.1 g (0.005 mole) of phosphorus pentachloride was held at reflux temperature for 4 hours. The product residue (from removal of volatiles) was dissolved in CH$_2$Cl$_2$, washed with water and chromatographed on Silica gel 40 (CH$_2$Cl$_2$ as eluent) to give 0.61 g (80%) of an oil. Cooling the oil gave the product, solid 2-(3-fluoro-3,3-dinitropropyl)-5-(perfluoropropyl)-1,3,4 -oxadiazole, mp 21°–22° C.; $^1$H NMR (CDC13): 3.15–3.75 (overlapping m).

Anal Calcd for C$_8$H$_4$F$_8$N$_4$O$_5$: C, 24.75; H, 1.04; F, 39.16; N, 14.43 Found: C, 24.66; H, 1.00; F, 38.80; N, 14.83.

EXAMPLE 11

N-(4-Fluoro-4,4-dinitrobutyryl)-N'-(perfluoropropionyl)hydrazine (5A)

To a solution of 0.95 g (0.0045 mole) of 4-fluoro-4,4-dinitrobutyryl chloride in 20 mL of anhydrous diethyl ether stirred at 20° C. was added 0.8 g (0.0045 mole) of N-(perfluoropropionyl)hydrazine followed by the dropwise addition of 0.4 mL of pyridine. After 5 minutes, dilute hydrochloric acid (10 mL) was added, the ether layer was separated, dried (Na$_2$SO$_4$) and the volatiles were removed to give the product N-(4-fluoro-4,4-dinitrobutyryl)-N'-(perfluoropropionyl)hydrazine, 1.05 g, mp 128°–132° C. Crystallization from 1,2-dichloroethane gave 0.93 g (58%), mp 135°–136° C. $^1$H NMR (acetone d$_6$+D$_2$O): 2.80 (t, 2H), 3.36, 3.58 (d of t, 2H).

EXAMPLE 12

2-(3-Fluoro-3,3-dinitropropyl)-5-(perfluoroethyl)-1,3,4-oxadiazole (5)

A mixture containing 0.7 g (0.002 mole) of N-(4-fluoro-4,4-dinitrobutyryl)-N'-(perfluoropropionyl)hydrazine and 1.0 g (0.005 mole) of phosphorus pentachloride in 7 mL of 1,2 -dichloroethane was heated at reflux temperature for 4 hours. Removal of volatiles gave a liquid residue which was dissolved in CH$_2$Cl$_2$, washed with water, and chromatographed on Silica gel 40 ( CH$_2$Cl$_2$ as eluent) to give 0.5 g (76%) of pure product as an oil. Cooling the oil gave the product, 2-(3-fluoro-3,3-dinitropropyl)-5-(perfluoroethyl)-1,3,4-oxadiazole, a solid, mp 3°–5° C.; $^1$H NMR (CDCl$_3$) 3.15–3.75 (overlapping m). Anal. Calcd for C$_7$H$_4$F$_6$N$_4$O$_5$: C, 24.86; H, 1.19; F, 33.71; N, 16.57. Found: C, 24.75; H, 1.22, F, 33.62; N, 16.57.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. An oxadiazole of the formula

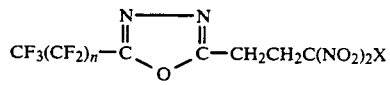

wherein X is —NO$_2$ or —F and wherein if X is —NO$_2$ then n is 0, 1, or 2, but if X is F then n is 0, 1, 2, 3, or 4.

2. An oxadiazole according to claim 1 wherein X is —NO$_2$.

3. The oxadiazole of claim 2 which is 2-(3,3,3-trinitropropyl)-5-(perfluoropropyl)-1,3,4-oxadiazole.

4. The oxadiazole of claim 2 which is 2-(3,3,3-trinitropropyl)-5-(perfluoroethyl)-1,3,4-oxadiazole.

5. The oxadiazole of claim 2 which is 2-(3,3,3-trinitropropyl)-5-(trifluoromethyl)-1,3,4-oxadiazole.

6. An oxadiazole according to claim 1 wherein X is —F.

7. The oxadiazole of claim 6 which is 2-(3-fluoro-3,3-dinitropropyl)-5-(perfluoropentyl)-1,3,4-oxadiazole.

8. The oxadiazole of claim 6 which is 2-(3-fluoro-3,3-dinitropropyl)-5-(perfluorobutyl)-1,3,4-oxadiazole.

9. The oxadiazole of claim 6 which is 2-(3-fluoro-3,3-dinitropropyl)-5-(perfluoropropyl)-1,3,4-oxadiazole.

10. The oxadiazole of claim 6 which is 2-(3-fluoro-3,3-dinitropropyl)-5-(perfluoroethyl)-1,3,4-oxadiazole.

11. The oxadiazole of claim 6 which is 2-(3-fluoro-3,3-dinitropropyl)-5-(trifluoromethyl)-1,3,4-oxadiazole.

* * * * *